United States Patent
Varga et al.

(10) Patent No.: US 8,631,798 B2
(45) Date of Patent: Jan. 21, 2014

(54) VALVING A RESPIRATORY GAS PATHWAY WITH A CATHETER BALLOON

(75) Inventors: Christopher M Varga, Laguna Hills, CA (US); Earl Valentine, Yorba Linda, CA (US); Thomas Dillingham, Aliso Viejo, CA (US); Alex Siemons, Yorba Linda, CA (US)

(73) Assignee: Carefusion 207, Inc., San Diego, CA (US)

( * ) Notice: Subject to any disclaimer, the term of this patent is extended or adjusted under 35 U.S.C. 154(b) by 207 days.

(21) Appl. No.: 13/075,099

(22) Filed: Mar. 29, 2011

(65) Prior Publication Data
US 2012/0247479 A1   Oct. 4, 2012

(51) Int. Cl.
*A61M 16/20*   (2006.01)

(52) U.S. Cl.
USPC .................. 128/207.16; 251/61.1; 138/93

(58) Field of Classification Search
USPC .................. 128/202.27, 203.11, 205.24, 128/207.14–207.16; 604/96.01–104; 138/93; 251/61.1
See application file for complete search history.

(56) References Cited

U.S. PATENT DOCUMENTS

| | | | |
|---|---|---|---|
| 4,020,849 A | 5/1977 | Jackson | |
| 4,787,408 A * | 11/1988 | Twerdochlib | 137/14 |
| 5,224,933 A * | 7/1993 | Bromander | 604/99.03 |
| 5,261,397 A | 11/1993 | Grunstein | |
| 5,348,270 A * | 9/1994 | Dinh | 251/61.1 |
| 5,477,886 A * | 12/1995 | Van Beugen et al. | 138/93 |
| 5,720,709 A | 2/1998 | Schnall | |
| 6,427,692 B1 | 8/2002 | Hoglund | |
| 2002/0103444 A1 * | 8/2002 | Ricciardelli | 600/532 |
| 2005/0217671 A1 * | 10/2005 | Fisher et al. | 128/204.18 |
| 2007/0062531 A1 * | 3/2007 | Fisher et al. | 128/204.23 |
| 2007/0062534 A1 * | 3/2007 | Fisher et al. | 128/205.14 |
| 2009/0241948 A1 | 10/2009 | Clancy et al. | |

OTHER PUBLICATIONS

International Search Report and Written Opinion for PCT/US2012/028960 mailed Oct. 31, 2012.

* cited by examiner

*Primary Examiner* — Loan Thanh
*Assistant Examiner* — Andrew S Lo
(74) *Attorney, Agent, or Firm* — McDermott Will & Emery LLP

(57) ABSTRACT

A respiratory valve device includes a catheter balloon configured for being disposed in a respiratory gas pathway and valving the respiratory gas pathway.

17 Claims, 4 Drawing Sheets

VALVING A RESPIRATORY GAS PATHWAY WITH A CATHETER BALLOON

BACKGROUND

Respiratory resting and/or therapy using a respiratory gas circuit or device typically requires, opening, closing, and/or isolating various breathing/respiratory gas paths. Traditional balloon technologies, used for these functions, are bulky and have a resistance to inflation due to elasticity. As a result, the traditional balloon technologies are very slow to inflate and deflate, and also cause high airflow resistance when deflated.

Butterfly valves or shutter-type valves are also utilized in respiratory testing. However, butterfly valves often exhibit leakage rates which render some respiratory measurement unreliable. Moreover, butterfly valves require electromechanical actuation which can be bulky and impractical to implement.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
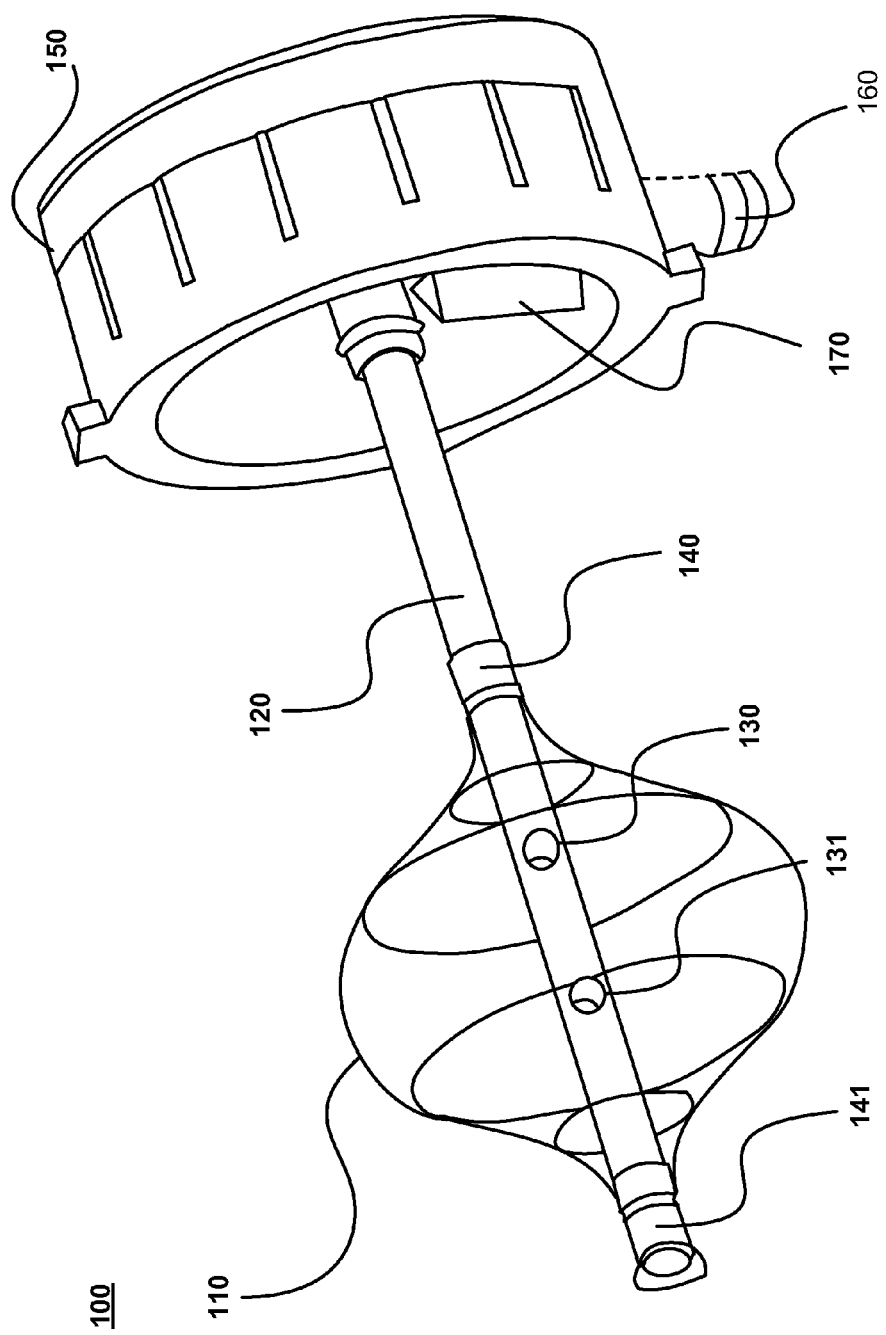
FIG. 1 illustrates an embodiment of a respiratory valve device.

FIG. 1 depicts an embodiment of respiratory valve device 100. Device 100 includes catheter balloon 110, stem 120, nozzles 130 and 131, collars 140 and 141, mount 150, gas connection 160 and stem base 170.

Catheter balloon 110 is configured for being disposed in a respiratory gas pathway and for valving the respiratory gas pathway. Embodiments described herein utilize a catheter balloon as a valving mechanism for opening, closing, and isolating of various breathing/respiratory gas paths while providing extremely low resistance to air flow in the deflated position.

A catheter balloon is traditionally used in surgical procedures (e.g., angioplasty) to enlarge narrow passages in the human body. A catheter balloon is manufactured in various sizes, shapes and materials. A catheter balloon is typically, extremely thin, but very strong under inflation. Accordingly, it is well suited for both (1) sealing against high and low pressures and (2) rapid inflation and deflations (in the order of milliseconds). Moreover, the thin structure of the catheter balloon enables it to collapse to a very small volume when deflated. Further, a catheter balloon utilized as a valving mechanism is very durable and has a long life time.

Catheter balloon 110 is disposed around stem 120 and nozzles 130 and 131. Catheter balloon 110 is fluidly sealed to stem 120 via collars 140 and 141.

To inflate catheter balloon 110, pressurized air (e.g., from a pump) flows through nozzles 130 and 131 of stem 120. In particular, the pressurized air flows through gas connection 160, stem base 170, stem 120 and out of nozzles 130 and 131.

When inflated, catheter balloon 110 completely occludes the respiratory gas pathway, such as a cylindrical tube of a respiratory circuit. In particular, the outer diameter of catheter balloon 110 fluidly seals with the inner diameter of the respiratory gas pathway.

To deflate catheter balloon 110, the catheter balloon is subjected to negative pressure, i.e., pressure below atmospheric pressure or partial vacuum. For example, a vacuum pump generates a negative pressure condition such that catheter balloon 110 is deflated.

When deflated, the catheter balloon 110 substantially conforms to the outer surface of stem 120. In other words, the inner surface of catheter balloon 110 mates with the outer surface of stem 120. Accordingly, a respiratory pathway gas flowing external to the catheter balloon 110 in the longitudinal direction of stem 120 is subjected to very little resistance from deflated catheter balloon 110.

It should be appreciated that at least one nozzle is provided on stem 120 to inflate and deflate (or evacuate) catheter balloon 110. However, any number of nozzles may be provided on stem 120 to inflate and deflate catheter balloon 110.

Mount 150 is configured to mount device 100 in a respiratory system. Such systems can be, but are not limited to, pulmonary function testing systems, cardiopulmonary exercise testing and metabolic systems, ventilators, and hand-held respiratory devices.

In one embodiment, mount 150 is in the form of a ring. In particular, stem 120 protrudes coaxially from the center of mount 150. When properly mated with a cylindrical tube or respiratory gas pathway, stem 120 and balloon 110 are coaxial with the cylindrical tube.

Mount 150 includes features such as aerodynamic surfaces that allow for low aft flow resistance when gases pass through mount 150 during a deflated state of balloon 110.

In one embodiment, stem base 170 is aerodynamic. For example, when airflow flows in the direction from collar 140 towards and through mount 150, stem base 170 is in a form such that it provides low resistance to the air flow.

Figure 2:
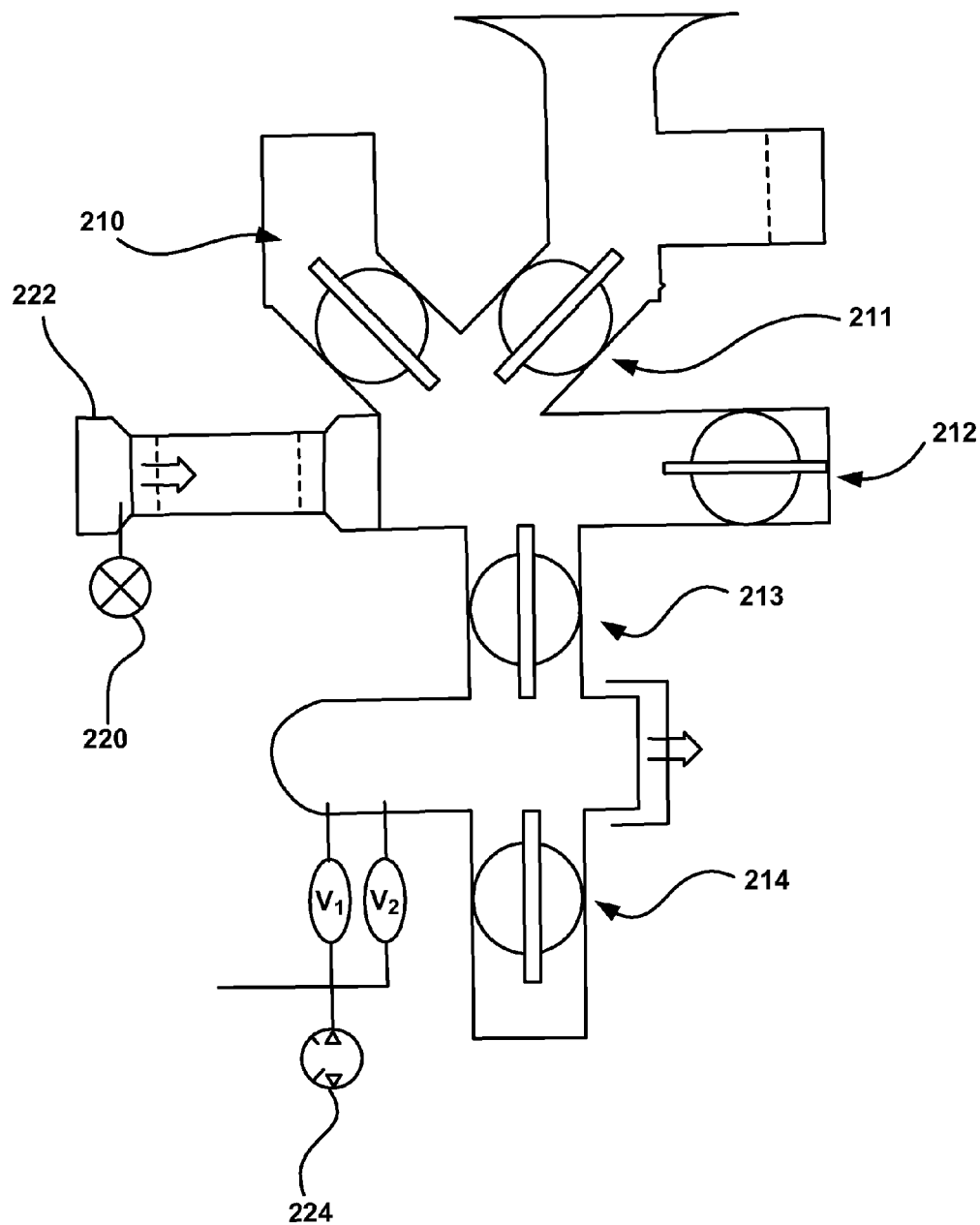
FIGS. 2 and 3 illustrate embodiments of a respiratory circuit.
Figure 3:
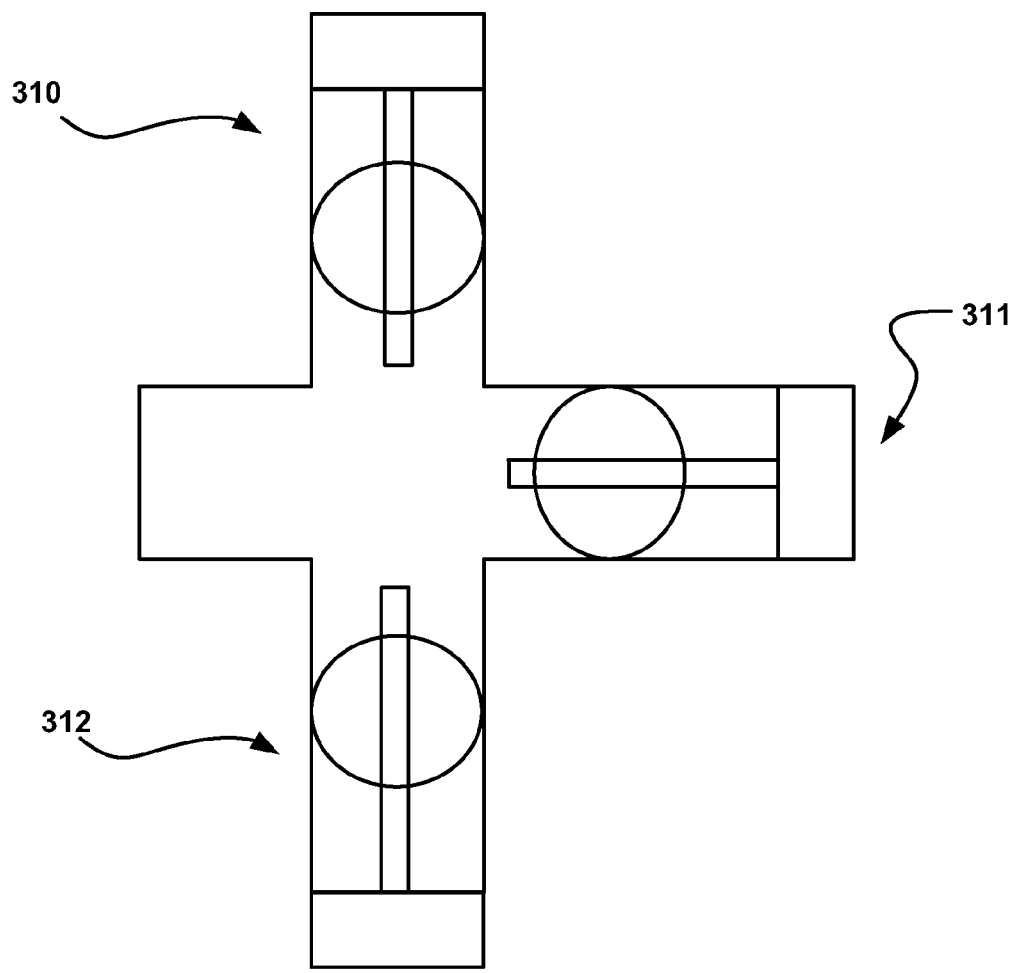

FIGS. 2 and 3 depict embodiments of respiratory circuits 200 and 300, respectively, incorporating a plurality of valving devices.

Referring now to FIG. 2, circuit 200 includes valving devices 210-214 disposed within a plurality of respiratory gas pathways. Valving devices 210-214 are similar to valving device 100, as described above.

It should be appreciated that circuit 200 includes a number of pathways for combining many different types of pulmonary measurements into a single instrument. For example, such measurements can be, but are not limited to, lung volume determination, inspiratory and expiratory flow rate, maximal inspiratory and expiratory pressure, airway resistance, airway conductance, respiratory impedance, reactance, and diffusion of different gases in and out of the lungs.

During use, a patient breathes through a mouthpiece 222 fluidly connected to the circuit 200. A pressure measurement port/location 220 is used to measure or monitor patient mouth pressure. Other sensors (e.g. for flow, temperature, etc.) may also be present in the circuit 200. Valving devices 210-214 can be inflated and deflated to perform different types of pulmonary measurements, as described above.

Although five devices 210-214 are depicted to occlude and/or isolate respiratory gas pathways, it should be appreciated that any number of respiratory valve devices can be disposed in the respiratory gas pathways of circuit 200.

In general, the catheter balloons of valving devices 210-214 are inflated during periods where the location of the assembly requires to be sealed. Valving devices 210-214 are deflated during periods where the location is required to be open for gas flow.

In various embodiments, the balloons and stems of devices 210-214 are in fluid communication with a set of one or more pressurized gas sources or reservoirs (e.g., gas sources V1 and V2), which are employed as drivers for the inflation and deflation of the catheter balloons.

The reservoirs are either kept at positive pressure for inflation or negative pressure (i.e. below atmospheric pressure) for deflation. Pumps (e.g., pump 224) or similar functionality is used to maintain the pressure of the reservoirs or can alternatively be used for direct filling or evacuating of the catheter balloons.

FIG. 3 depicts an embodiment of circuit 300 which includes valving devices 310-312 disposed within a plurality of respiratory gas pathways. Circuit 300 is similar to circuit 200. However, circuit 300 includes three valving devices and includes different respiratory gas pathways. Valving devices 310-312 are similar to valving device 100, as described above.

Figure 4:
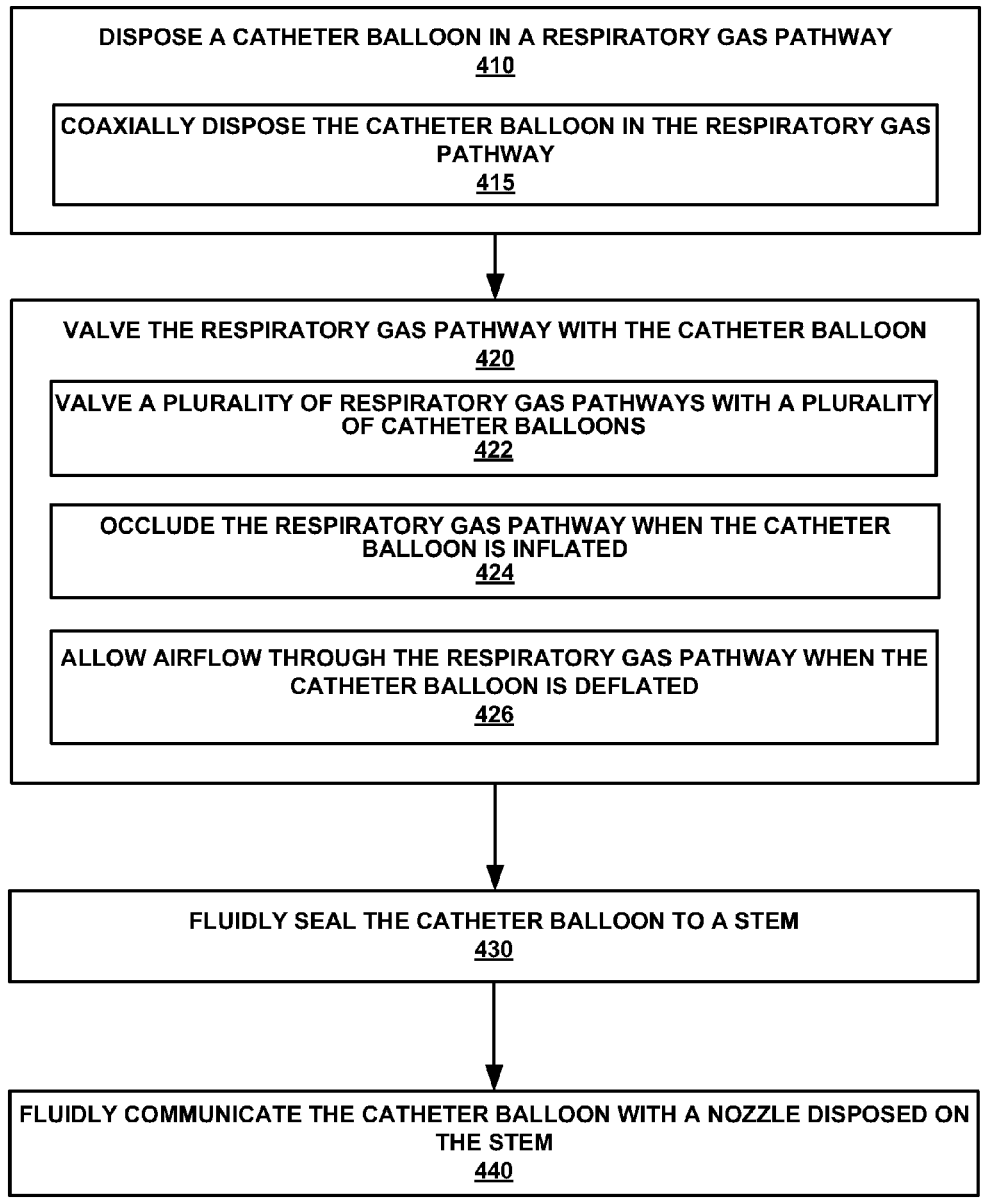
FIG. 4 illustrates an embodiment of a method for valving a respiratory circuit.

FIG. 4 depicts an embodiment of a method 400 for valving a respiratory circuit. In various embodiments, method 400 is performed at least by device 100, as described in FIG. 1.

At 410 of method 400, a catheter balloon is disposed in a respiratory gas pathway. For example, catheter balloon 110 is disposed in a respiratory gas pathway of circuits 200 or 300.

In one embodiment, at 415, the catheter balloon is coaxially disposed in the respiratory gas pathway. For example, catheter balloon 110 is coaxially disposed in a respiratory gas pathway of circuits 200 or 300.

At 420, the respiratory gas pathway is valved with the catheter balloon.

In one embodiment, at 422, a plurality of respiratory gas pathways are valved with a plurality of catheter balloons. For example, catheter balloons associated with valving devices 210-214 valve a plurality of associated respiratory gas pathways of circuit 200.

In another embodiment, at 424, the respiratory gas pathway is occluded when the catheter balloon is inflated. For example, when catheter balloon 110 is inflated, it fluidly seals the respiratory gas pathway.

In another embodiment, at 426, airflow through the respiratory gas pathway is allowed when the catheter balloon is deflated. For example, catheter balloon 110 conforms to the shape of the outside surface of stem 120, when deflated. Accordingly, airflow is allowed through the respiratory gas pathway with little resistance.

At 430, the catheter balloon is fluidly sealed to a stem. For example, collars 140 and 141 fluidly seal catheter balloon 110 to stem 120.

At 440, the catheter balloon fluidly communicates with a nozzle disposed on the stem. For example, catheter balloon 110 is inflated/deflated due to the fluid communication with nozzles 130 and 131 disposed on stem 120.

It should be noted that the various embodiments described herein can be used in combination with one another. That is one described embodiment can be used in combination with one or more other described embodiments.

Various embodiments of the present invention are thus described. While the present invention has been described in particular embodiments, it should be appreciated that the present invention should not be construed as limited by such embodiments, but rather construed according to the following claims.

The invention claimed is:

1. A respiratory valve device comprising:
a catheter balloon configured for being disposed in a respiratory gas pathway and valving said respiratory gas pathway;
a stem comprising a nozzle, wherein said catheter balloon is disposed around said stem and said nozzle;
a ring mount configured for placement of said catheter balloon within said respiratory gas pathway, the stem protruding coaxially from a center of the mount; and
an aerodynamic stem base arranged on the mount perpendicular to the stem, the stem base being in fluid communication with the stem and nozzle.

2. The respiratory valve device of claim 1, wherein said catheter balloon is further configured to occlude said respiratory gas pathway when inflated.

3. The respiratory valve device of claim 1, wherein said catheter balloon is further configured to allow air flow through said respiratory gas pathway when deflated.

4. The respiratory valve device of claim 1, wherein said stem is coaxial with said respiratory gas pathway.

5. The respiratory valve device of claim 1, further comprising:
a stem comprising a plurality of nozzles, wherein said catheter balloon is disposed around said stem and said plurality of nozzles.

6. The respiratory valve device of claim 1, further comprising:
a collar configured to fluidly seal said catheter balloon to a stem.

7. A respiratory circuit comprising:
a plurality of catheter balloons disposed in a plurality of respiratory gas pathways and configured for valving said respiratory gas pathways;
wherein the plurality of catheter balloons each comprise:
a stem comprising a nozzle, wherein each one of the plurality of catheter balloons is disposed around a corresponding stem and nozzle;
a ring mount configured for placement of each one of the plurality of catheter balloons within the plurality of respiratory gas pathways, the stem protruding coaxially from a center of the mount; and
an aerodynamic stem base arranged on the mount perpendicular to the stem, the stem base being in fluid communication with the stem and nozzle.

8. The respiratory circuit of claim 7 configured for performing a plurality of pulmonary measurements selected from a group consisting of: lung volume, inspiratory flow rate, expiratory flow rate, inspiratory pressure, expiratory pressure, airway resistance, airway conductance, respiratory impedance, reactance, or diffusion of gases in and out of lungs.

9. The respiratory circuit system of claim 7, wherein said plurality of catheter balloons are further configured to occlude said respiratory gas pathways when inflated.

10. The respiratory circuit system of claim 7, wherein said plurality of catheter balloons are further configured to allow air flow through said plurality of respiratory gas pathways when deflated.

11. A method for valving a respiratory circuit, said method comprising:
 disposing a catheter balloon in a respiratory gas pathway; and
 valving said respiratory gas pathway with said catheter balloon,
 wherein the catheter balloon comprises:
  a stem comprising a nozzle, wherein said catheter balloon is disposed around said stem and said nozzle;
  a ring mount configured for placement of said catheter balloon within said respiratory gas pathway, the stem protruding coaxially from a center of the mount; and
  an aerodynamic stem base arranged on the mount perpendicular to the stem, wherein the stem base is in fluid communication with said stem and nozzle.

12. The method of claim 11, wherein said disposing a catheter balloon in a respiratory gas pathway further comprises:
 coaxially disposing said catheter balloon in said respiratory gas pathway.

13. The method of claim 11, wherein said valving said respiratory gas pathway with said catheter balloon comprises:
 valving a plurality of respiratory gas pathways with a plurality of catheter balloons.

14. The method of claim 11, wherein said valving said respiratory gas pathway with said catheter balloon comprises:
 occluding said respiratory gas pathway when said catheter balloon is inflated.

15. The method of claim 11, wherein said valving said respiratory gas pathway with said catheter balloon comprises:
 allowing airflow through said respiratory gas pathway when said catheter balloon is deflated.

16. The method of claim 11, further comprising:
 fluidly sealing said catheter balloon to the stem.

17. The method of claim 16, further comprising:
 fluidly communicating said catheter balloon with the nozzle disposed on said stem.

* * * * *